United States Patent [19]

Takaya et al.

[11] 4,363,807
[45] Dec. 14, 1982

[54] CEPHAM COMPOUNDS

[75] Inventors: Takao Takaya, Kawanishi; Takashi Masugi, Toyonaka; Toshiyuki Chiba, Osaka, all of Japan

[73] Assignee: Fujisawa Pharmaceutical Company, Limited, Osaka, Japan

[21] Appl. No.: 103,821

[22] Filed: Oct. 17, 1979

[30] Foreign Application Priority Data

Oct. 17, 1978 [JP] Japan .................................. 53-40789

[51] Int. Cl.³ .................. C07D 501/20; A61K 31/545
[52] U.S. Cl. ..................................... 424/246; 544/16; 544/28; 544/30; 544/22
[58] Field of Search ...................... 544/16, 30, 26, 270, 544/28, 22, 27; 424/246

[56] References Cited

U.S. PATENT DOCUMENTS

| | | | |
|---|---|---|---|
| 3,674,784 | 7/1972 | Webber | 544/16 |
| 4,152,432 | 5/1979 | Heymes et al. | 424/246 |
| 4,166,115 | 8/1979 | Takaya et al. | 424/246 |
| 4,248,868 | 2/1981 | Scartazzini et al. | 544/16 |

Primary Examiner—Nicholas S. Rizzo

Attorney, Agent, or Firm—Oblon, Fisher, Spivak, McClelland & Maier

[57] ABSTRACT

This invention relates to novel cepham compounds of antimicrobial activity, useful as intermediates in the preparation of antibiotics, said novel cepham compounds being of the formula:

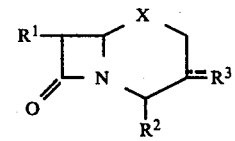

wherein
$R^1$ is phenyl (lower) alkanoylamino, phenoxy (lower) alkanoylamino or aminothiazolyl (lower) alkanoylamino substituted with a lower alkoxyimino group,
$R^2$ is carboxy or a protected carboxy group,
$R^3$ is formyl, hydroxymethyl or acyloxymethylene, and
X is —S— or —SO—, and its salt.

9 Claims, No Drawings

CEPHAM COMPOUNDS

This invention relates to novel cepham compounds and the processes for preparation thereof. More particularly, this invention relates to novel 3,7-disubstituted cepham-4-carboxylic acid compounds (I) and pharmaceutically acceptable salt thereof and the processes for preparing thereof, which have antimicrobial activities and are useful as antibiotics, and also useful as intermediates for manufacturing other potential antibiotics, for example, 7-acylamino-3-cephem-4-carboxylic acid.

The object 3,7-disubstituted cepham-4-carboxylic acid compounds are novel and can be represented by the following formula (I).

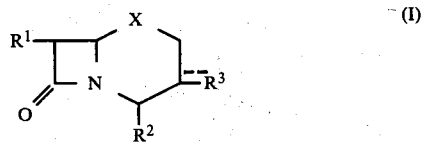

wherein
$R^1$ is amino or a protected amino group,
$R^2$ is carboxy or a protected carboxy group,
$R^3$ is formyl, hydroxymethyl or acyloxymethylene and
X is —S— or —SO—.

The processes of the present invention can be illustrated by the following schemes.

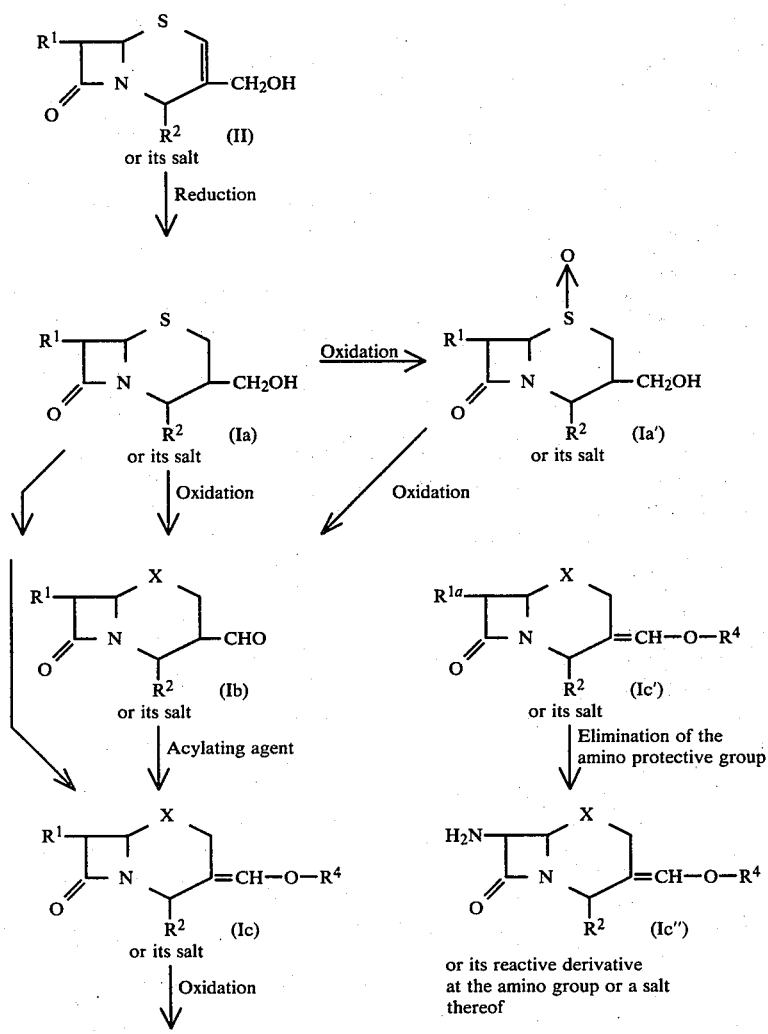

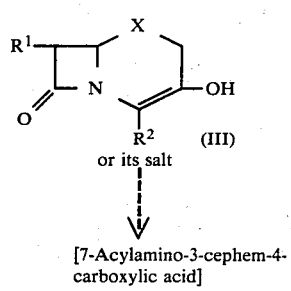

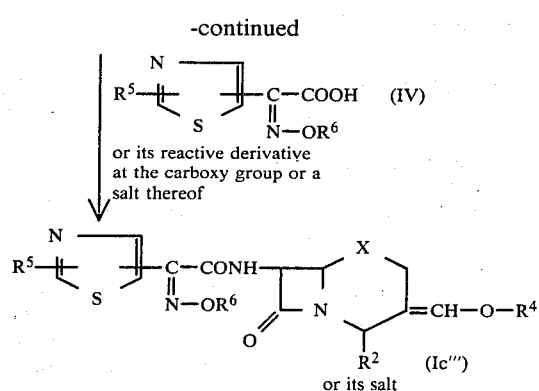

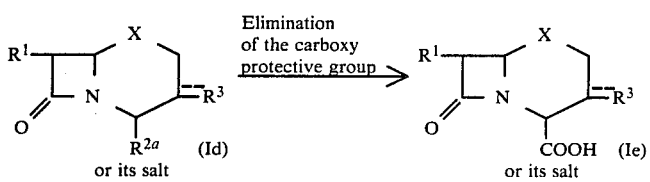

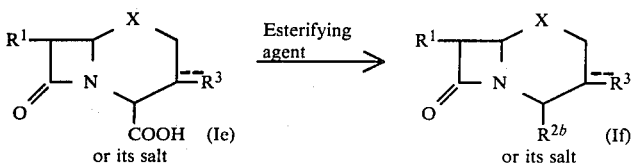

wherein
R$^1$, R$^2$, R$^3$ and X are each as defined above, R$^{1a}$ is a protected amino group,
R$^{2a}$ is a protected carboxy group,
R$^{2b}$ is an esterified carboxy group,
R$^4$ is acyl,
R$^5$ is amino or a protected amino group and
R$^6$ is lower alkyl.

Suitable salts of the compounds (I), (II), (III) and (IV) may be conventional ones, and may include a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like.

According to prior methods, the compound (IIIa) is prepared by (1) reducing the compound (VI) to produce a mixture of the compounds (VII) and (VIII), and (ii) isolating the compound (VII) from the said mixture and then (iii) oxidizing the compound (VII) as shown in the following reaction scheme.

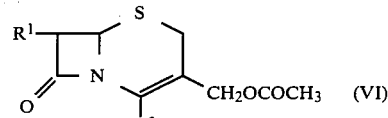

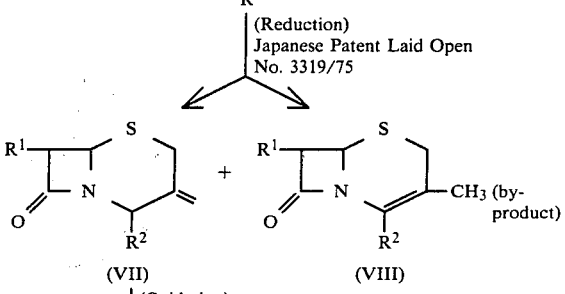

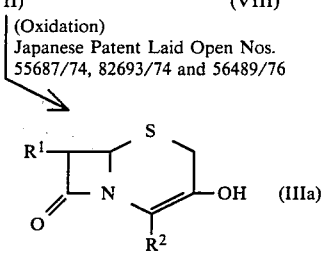

wherein R$^1$ and R$^2$ and each as defined above.

However, according to the above prior methods, a large quantity of the compound (VIII) is produced as a by-product which can not be led to the compound (IIIa), and it is very difficult to isolate the desired compound (VII) from the reaction mixture of the compounds (VII) and (VIII) due to the similar physical properties of the compounds (VII) and (VIII).

While, according to the present invention, the compound (III) can be prepared without such demerits.

In the above and subsequent descriptions of this specification, suitable examples and illustration of the various definitions which this invention intends to include within the scope thereof are explained in detail as follows.

The term "lower" is used to intend a group having 1 to 6 carbon atom(s), unless otherwise provided.

Suitable "lower alkyl" may include methyl, ethyl, propyl, isopropyl, butyl, pentyl, hexyl and the like.

Suitable "protected amino group" may include an amino group substituted by a conventional aminoprotective group such as acyl as mentioned below, ar(lower)alkyl (e.g. benzyl, benzhydryl, trityl, etc.) and the like.

Suitable "acyl" and "acyl moiety" in the term "acyloxymethylene" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, etc.), lower alkenoyl (e.g. acryloyl, methacryloyl, crotonoyl, etc.), ($C_3$–$C_7$)-cycloalkanecarbonyl (e.g. cyclohexanecarbonyl, etc.). The aromatic acyl may include aroyl (e.g. benzoyl, toluoyl, xyloyl, etc.), arenesulfonyl (e.g. benzenesulfonyl, tosyl, etc.), and the like. The heterocyclic acyl may include heterocycle carbonyl (e.g. furoyl, thenoyl, nicothinoyl, isonicotinoyl, thiazolylcarbonyl, thiadiazolylcarbonyl, tetrazolylcarbonyl, etc.). The aliphatic acyl substituted with aromatic group(s) may include phenyl(lower)alkanoyl (e.g. phenylacetyl, phenylpropionyl, phenylhexanoyl, etc.). The aliphatic acyl substituted with heterocyclic group(s) may be thienylacetyl, imidazolylacetyl, furylacetyl, tetrazolylacetyl, thiazolylacetyl, thiadiazolylacetyl, thienylpropionyl, thiadiazolylpropionyl, or the like. These acyl groups may be further substituted with one or more suitable substituents such as carboxy, amino, a protected amino group, cyano, hydroxy, oxo, lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.) lower alkylthio (e.g. methylthio, ethylthio, propylthio, isopropylthio, butylthio, pentylthio, hexylthio, etc.), lower alkoxyimino (e.g. methoxyimino, ethoxyimino, etc.) and the like, and preferable acyl having such substituent(s) may be 5-amino-5-carboxyvaleryl, in which the amino moiety may be protected with an acyl such as halo(lower)alkanoyl (e.g. α-chloroacetyl, α,α-dichloropropionyl, α,α-dibromobutyryl, etc.), aroyl (e.g. phthaloyl, benzoyl, etc.), carbamoyl substituted with a lower alkyl or phenyl or halogen (e.g. ethylcarbamoyl, phenylcarbamoyl, 4-chlorophenylcarbamoyl, etc.), lower alkoxycarbonyl (e.g. t-butoxycarbonyl, etc.), isobornyloxycarbonyl, and the like.

Suitable "protected carboxy group" may be an esterified carboxy group, an amidated carboxy group or the like.

Suitable "ester moiety" in "esterified carboxy group" may be a conventional one such as lower alkyl ester (e.g. methyl ester, ethyl ester, propyl ester, isopropyl ester, butyl ester, isobutyl ester, t-butyl ester, pentyl ester, t-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester, isopropylthiomethyl ester, etc.), halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, palmitoyloxymethyl ester, etc.), lower alkanesulfonyl(lower)alkyl ester (e.g. mesylmethyl ester, 2-mesylethyl ester, etc.), phenyl(lower)alkyl ester which may have one or more suitable substituent(s) (e.g. benzyl ester, 4-methoxybenzyl ester, 4-nitrobenzyl ester, phenethyl ester, diphenylmethyl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), an ester with a silyl compound such as tri(lower)alkylsilyl compound, di(lower)alkyl(lower)alkoxysilyl compound or tri(lower)alkoxysilyl compound, for example, tri(lower)alkylsilyl ester (e.g. trimethylsilyl ester, triethylsilyl ester, etc.), di(lower)alkyl(loweralkoxysilyl ester (e.g. dimethylmethoxysilyl ester, dimethylethoxysilyl ester, diethylmethoxysilyl ester, etc.) or tri(lower)alkoxysilyl ester (e.g. trimethoxysilyl ester, triethoxysilyl ester, etc.) or the like.

More particularly, the preferable examples of $R^1$, $R^{1a}$, $R^2$, $R^{2a}$, $R^{2b}$, $R^3$, $R^4$, $R^5$ and $R^6$ are illustrated as follows.

The preferable examples of $R^1$ may be amino or acylamino, more preferably phenyl(lower)alkanoylamino (e.g. phenylacetamido, phenylpropionamide, etc.), phenoxy(lower)alkanoylamino (e.g. phenoxyacetamido, phenoxypropionamido, etc.), aminothiazolyl(lower)alkanoylamino substituted with a lower alkoxyimino group [e.g. 2-(2-aminothiazol-4-yl)-2-methoxyiminoacetamido, etc.] and the like.

The preferable examples of $R^{1a}$ may be phenyl(lower)alkanoylamino (e.g. phenylacetamido, phenylpropionamido, etc.), phenoxy(lower)alkanoylamino (e.g. phenoxyacetamido, etc.) and the like.

The preferable examples of $R^2$ may be carboxy, an esterified carboxy group such as lower alkoxycarbonyl (e.g. methoxycarbonyl, ethoxycarbonyl, propoxycarbonyl, t-butoxycarbonyl, etc.), mono(or di or tri)phenyl(lower)alkoxycarbonyl (e.g. benzyloxycarbonyl, diphenylmethoxycarbonyl, trityloxycarbonyl, etc.), nitrophenyl(lower)alkoxycarbonyl (e.g. 4-nitrobenzyloxycarbonyl, etc.). The preferable examples of $R^{2a}$ and $R^{2b}$ may be an esterified carboxy group as illustrated for $R^2$.

The preferable examples of $R^3$ may be formyl, hydroxymethyl, lower alkanoyloxymethylene (e.g. formyloxymethylene, acetoxymethylene, propionyloxymethylene, etc.) and the like.

The preferable examples of $R^4$ may be lower alkanoyl (e.g. formyl, acetyl, propionyl, etc.) and the like.

The preferable examples of $R^5$ may be amino or acylamino [more preferably, lower alkanoylamino (e.g. formamido, acetamido, etc.)] and the like.

The preferable examples of $R^6$ may be methyl, ethyl and propyl, and most preferably methyl.

Each process of this invention is explained in detail in the following.

PROCESS 1

The compound (Ia) or its salt can be prepared by reducing a compound (II) or its salt.

The starting compound (II) or its salt is known compound and can be prepared, for example, by reacting a compound (a) with borontrihalide and then treating the resultant compound with water as illustrated below.

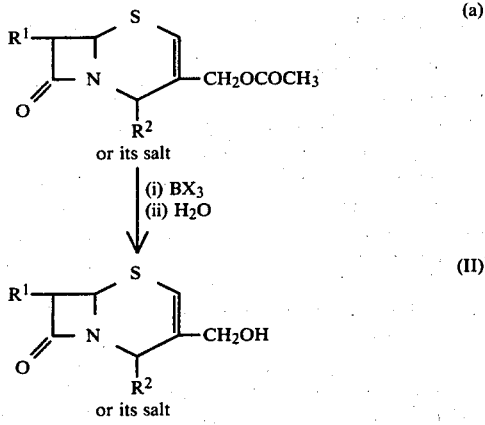

wherein X is halogen, and $R^1$ and $R^2$ are each as defined above.

The reduction reaction of the compound (II) or its salt may be a conventional one which can trasform a 2-cephem compound to a cepham compound, and preferable method may be reduction using a combination of an acid (e.g. hydrochloric acid, sulfuric acid, formic acid, acetic acid, etc.), and metal (e.g. zinc, iron, copper, etc.), amalgamated metals such as sodium amalgam, zinc amalgam and aluminum amalgam, bimetallic couples such as the zinc-copper couples, and the salts of oxidizable metals, for example, chromous chloride, chromous bromide, chromous acetate and the like; a conventional catalytic reduction using a conventional catalyst (e.g. palladium on carbon, palladium sponge, Raney nickel, platinum, platinum black, platinum oxide, rhodium on carbon or alumina, ruthenium carbon, rhodium (I) complexes of the Wilkinson type, etc.) or the like.

The reaction is usually carried out in a conventional solvent such as water, alcohol (e.g. methanol, ethanol, etc.), N,N-dimethylformamide, tetrahydrofuran or any other solvent which does not adversely influence the reaction. The reaction temperature is not critical, and the reaction can be preferably carried out under cooling to somewhat elevated temperature.

PROCESS 2

The compound (Ia′) and its salt can be prepared by oxidizing agent (Ia) or its salt by a conventional method which is applicable for transforming a "—S—" group into a "—SO—" group.

PROCESS 3

The compound (Ib) or its salt can be prepared by oxidizing a compound (Ia) or (Ia′) or a salt thereof.

The oxidation reaction may be a conventional one which is applicable for transforming a hydroxymethyl group into a formyl group, and may preferably be conducted by using a strong oxidizing agent such as chromium compound or its salt (e.g. chromium oxide, sodium dichromate, potassium chromate, chromium oxide-pyridine complex, etc.), manganese compound or its salt (e.g. manganese dioxide, potassium manganate, sodium manganate, potassium permanganate, etc.), halogen (e.g. bromine, etc.), and the like, copper compound (e.g. cupric sulfate, etc.), silver compound (e.g. silver oxide, etc.); a combination of an aldehyde or ketone (e.g. acetone, etc.) and an alkali metal alkoxide (e.g. sodium tert-butoxide, etc.) or an aluminum alkoxide (e.g. aluminum isopropoxide, etc.); a N-halogenated imide (e.g. N-bromosuccinimide, N-chlorosuccinimide, etc.); a combination of a carbodiimide (e.g. N,N-dicyclohexylcarbodiimide, etc.) and dimethylsulfoxide; or the like. In case of using a combination of a carbodiimide and dimethylsulfoxide, the reaction is preferably conducted in the presence of a base (e.g. pyridine, triethylamine, etc.), a rather strong acid such as an inorganic acid (e.g. hydrochloric acid, etc.), an organic carboxylic or sulfonic acid such as haloalkanoic acid (e.g. trifluoroacetic acid, dichloroacetic acid, etc.), alkanesulfonic acid (e.g. methanesulfonic acid, etc.), arenesulfonic acid (e.g. benzenesulfonic acid, p-toluenesulfonic acid, etc.), or the like.

These reaction may usually be carried out in a solvent such as benzene, chloroform, methylene chloride, tetrahydrofuran, methanol, ethanol or the other solvent which does not adversely influence the reaction. The reaction temperature is not critical and the reaction can preferably be carried out under cooling to heating.

It is to be noted that the reaction product (Ib) includes the corresponding tautomeric enol as shown by the following structures.

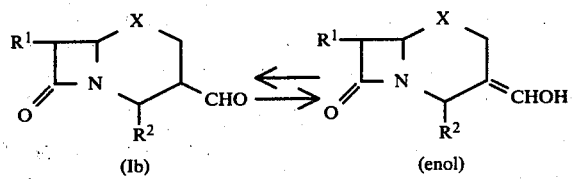

when the present oxidation reaction is conducted in the presence of an acylating agent, the compound (Ic) can be obtained directly.

PROCESS 4

The compound (Ic) or its salt can be prepared by reacting a compound (Ib) or a salt thereof with an acylating agent. Suitable acylating agent may include an acid of the formula: Acyl-OH(V) or its reactive derivative at the carboxy group or a salt thereof.

Suitable reactive derivative at the carboxy group may include, for example, an acid halide, an acid anhydride, an activated amide, an activated ester, and the like, and preferably acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.);

a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivatives of the compound (V) can optionally be selected from the above according to the kind of the compound (V) to be used practically, and to the reaction conditions.

Suitable salt of the compound (V) may include a salt with an inorganic base such as alkali metal salt (e.g. sodium salt, potassium salt, etc.) and an alkaline earth metal salt (e.g. calcium salt, magnesium salt, etc.), a salt with an organic base such as tertiary amine (e.g., trimethylamine salt, triethylamine salt, N,N-dimethylaniline salt, pyridine salt, etc.) and the like.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction or an optional mixture thereof.

When the acylating agent is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazole compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of N,N-dimethylformamide with thionyl chloride, phosphorus oxychloride, phosgene or the like. The present reaction temperature is not critical and the reaction can be preferably carried out under cooling to heating.

When the compound (Ib) wherein $R^1$ is amino or its salt is used as a starting material in this process, the said 7-amino group is occasionally acylated, and such case is also included in this process.

PROCESS 5

The compound (Ic″) or its salt can be prepared by subjecting a compound (Ic′) or its salt, to elimination reaction of the protective group of the amino.

The elimination reaction may be conducted in accordance with a conventional method such as hydrolysis, reduction or the like. These methods may be selected according to the kind of the protective group to be eliminated.

The hydrolysis may include a method using an acid (acidic hydrolysis), a base (basis hydrolysis) or hydrazine, and the like.

Among these methods, hydrolysis using an acid is one of the common and preferable methods for eliminating the protective group such as an acyl group, for example, substituted or unsubstituted lower alkanoyl, substituted or unsubstituted lower alkoxycarbonyl, substituted or unsubstituted ar(lower)alkoxycarbonyl, lower cycloalkoxycarbonyl, substituted phenylthio, substituted alkylidene, substituted aralkylidene, substituted cycloalkylidene or the like. Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound (Ic′) and the product (Ic″) as well as the kind of the protective group to be eliminated. The acidic hydrolysis can be conducted in the presence or absence of a solvent. Suitable solvent may be a conventional organic solvent, water or a mixture thereof, which does not adversely influence this reaction. The acidic hydrolysis using trifluoroacetic acid is usually accelerated by addition of anisole.

The hydrolysis using a base can be applied for eliminating the protective group such as an acyl group, preferably, for example, haloalkanoyl (e.g. trifluoroacetyl, etc.) and the like. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2]octane, 1,5-diazabicyclo[5,4,0]-7-undecene, anion-exchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reduction can be applied for eliminating the protective group such as acyl group, for example, halo(lower)alkoxycarbonyl (e.g. trichloroethoxycarbonyl, etc.), substituted or unsubstituted ar(lower)alkoxycarbonyl (e.g. benzyloxycarbonyl, p-nitrobenzyloxycarbonyl, 2-pyridylmethoxycarbonyl, etc., aralkyl (e.g. benzyl, benzhydryl, trityl, etc.) and the like. Suitable reduction may include, for example, reduction using an alkali metal borohydride (e.g. sodium borohydride, etc.), conventional catalytic hydrogenolysis and the like.

And further, the protective group such as halo(lower)alkoxycarbonyl or 8-quinolyloxycarbonyl can be eliminated by treatment with a heavy metal such as copper, zinc or the like.

Additionally, the acyl group can also be eliminated by treating with an iminohalogenating agent (e.g. phosphorus oxychloride, etc.) and an imino-etherifying agent such as lower alkanol (e.g. methanol, ethanol, etc.), if necessary, followed by hydrolysis.

The reaction temperature is not critical and may optionally be selected in consideration of the chemical property of the starting compound and reaction product as well as the kind of the N-protective group and the method to be applied, and the reaction is preferably carried out under a mild condition such as under cooling, at ambient temperature or slightly elevated temperature.

And further this process includes in its scope the cases tht the protected carboxy and $R^2$ is simultaneously transformed into the free carboxy group in the course of the above reaction or in the post-treatment.

PROCESS 6

The compound (Ic''') or its salt can be prepared by reacting the compound (Ic''), or its reactive derivative at the amino group or a salt thereof with a compound (IV) or its reactive derivative at the carboxy group or a salt thereof.

Suitable reactive derivative at the amino group of the compound (Ic'') may include a conventional reactive derivative as used in a wide variety of amidation reaction, for example, isocyanato, isothiocyanato, a derivative formed by the reaction of a compound (Ic'') with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with ketone compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorus chloride, etc.), or with a sulfur compound (e.g. thionyl chloride, etc.), and the like.

Suitable reactive derivative at the carboxy group of the compound (IV) may include, for example, an acid halide, an acid anhydride, an activated amide, an activated ester, and the like, and preferably acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivatives of the compounds (IV) can optionally be selected from the above according to the kind of the compounds (IV) to be used practically, and to the reaction conditions.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction or an optional mixture thereof.

When the acylating agent (IV) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of dimethylformamide with thionyl chloride, phosphorus oxychloride, phosgene or the like. The reaction temperature is not critical, and the reaction can preferably be carried out under cooling to warming.

PROCESS 7

The compound (Ie) or its salt can be prepared by subjecting the compound (Id) or its salt, to elimination reaction of the protective group of the carboxy.

The method to be applied to this process includes conventional ones such as hydrolysis, reduction and the like.

The method of hydrolysis includes a conventional one using an acid, base, and the like.

Suitable examples of the acid and base are to be referred to those as exemplified in the above Process 5, and the acidic or basic hydrolysis can be carried out in a similar manner to that of the Process 5.

The method of the reduction for this process may be carried out in a similar manner to that of the above Process 5.

PROCESS 8

The compound (If) or its salt can be prepared by reacting the compound (Ie) or its salt with an esterifying agent.

Suitable esterifying agent may include a hydroxy compound and its reaction equivalent.

Suitable examples of the hydroxy compound may be a lower alkanol (e.g. methanol, ethanol, propanol, tert-butyl alcohol, etc.), a diphenyl(lower)alkanol (e.g. diphenylmethanol, etc.), a nitrophenyl(lower)alkanol (e.g. 4-nitrobenzyl alcohol, etc.) or the like.

Suitable reactive equivalent of the hydroxy compound may include a conventional one such as a halide (e.g. bromide, iodide, etc.), a diazo compound, or the like.

The reaction can be carried out in the presence or absence of a solvent such as N,N-dimethylformamide, tetrahydrofuran, ethyl acetate, dimethylsulfoxide or any other solvent which does not adversely influence the reaction. The reaction temperature is not critical, and the reaction may preferably be conducted under cooling to heating. The liquid hydroxy compound can also be used as a solvent in this reaction.

This reaction can preferably be conducted in the presence of an inorganic or organic base as exemplified in the above Process 5.

PROCESS 9

The compound (III) or its salt can be prepared by reacting the compound (Ic) or its salt with an oxidizing agent which is applicable to oxidative cleavage of carbon-carbon double bond. Suitable oxidizing agent may be ozone or a metal compound such as a manganese compound (e.g. potassium permanganate, sodium permanganate, etc.), an osmium compound (e.g. osmium tetroxide, etc.) and the like.

In case that ozone is used as an oxidizing agent, it is necessary to treat the resultant compound (i.e. ozonide) with a reducing agent as exemplified in the Process 1 or a boron compound (e.g. sodium boronhydride, diboran, etc.), or di(lower)alkyl sulfide (e.g. dimethylsulfide, etc.).

The reaction is preferably conducted in a solvent such as lower alkanol (e.g. methanol, ethanol, propanol, butanol, pentanol, hexanol, etc.), chloroform, methylene chloride, acetone, tetrahydrofuran, benzene, diethyl ether, N,N-dimethylformamide, or any other solvent which does not adversely influence the reaction. The reaction temperature is not critical and the reaction can preferably be carried out under cooling to heating. The compound (III) wherein X is —SO— may occasionally be obtained from the compound (Ic) wherein X is —S— by this process according to the reaction condition, and such case is also included in this process.

The compound (III) is in equilibrium as illustrated below:

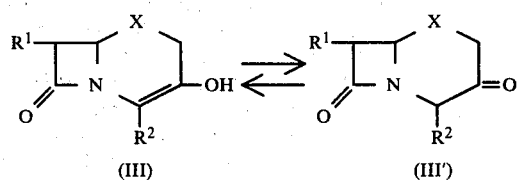

wherein $R^1$, $R^2$ and X are each as defined above.

Both of these tautomers (III) and (III') are included within the scope of this process.

The object compound (I) and its pharmaceutically acceptable salt exhibit high antimicrobial activities inhibiting the growth of a wide variety of pathogenic microorganisms including Gram-positive and Gram-negative bacteria and are useful as antimicrobial agents.

In order to show the utility of the compound (I) the test data of the representative compound (I) are shown in the following.

1. In vitro antibacterial activity:
   (1) Test method:

In vitro antibacterial activity was determined by the two-fold agar-plate dilution method as described below.

One loopful of an overnight culture of each test strain in Trypticase soy broth was streaked on heart infusion agar (HI-agar) containing graded concentration of the test compound and incubated at 37° C. for 20 hours. The minimal inhibitory concentration (MIC) was expressed in μg/ml.

(2) Test compound:
7-[2-(2-Aminothiazol-4-yl)-2-methoxyiminoacetamido]-3-acetoxymethylenecepham-4-carboxylic acid (syn isomer).

(3) Test results:

| Test strains | MIC (μg/ml) Test compound |
|---|---|
| Klebsiella pneumoniae 20 | 6.25 |
| Proteus mirabilis 18 | 6.25 |

For prophylactic and/or therapeutic administration, the compound (I) of the present invention is used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age and conditions of the patient, a kind of disease and a degree of the infection, and further a kind of the active compound (I) to be applied, etc., an average single dose of about 50 mg., 100 mg., 250 mg. and 500 mg. of the active compound (I) is sufficient for treating infectious diseases caused by pathogenic bacteria. In general, the active compound (I) can be administered in an amount between 1 mg/kg and 100 mg/kg, preferably 5 mg/kg and 50 mg/kg.

The object compound (I) and its salt are also useful as an intermediate for manufacturing other potential antibiotics, for example, 7-acylamino-3-cephem-4-carboxylic acid or its salt which can be prepared by leading the object compound (I) or its salt to the compound (III) or its salt as aforementioned and then leading the compound (III) or its salt to 7-acylamino-3-cephem-4-carboxylic acid or its salt as described in DT-OS No. 2.810.922.

The present invention is explained in more detail by the following examples.

EXAMPLE 1

(1) A suspension of 10% palladium carbon (16 g) in acetic acid (50 ml) was added to a solution of t-butyl 7-(2-phenylacetamido)-3-hydroxymethyl-2-cephem-4-carboxylate (9.0 g) in ethanol (300 ml.), and the mixture was subjected to catalytic reduction at 65° C. in the presence of hydrogen at 20 atm. for 9 hours. After removing the insoluble substance by filtration, the filtrate was concentrated in vacuo. The residue was dissolved in ethyl acetate (150 ml.) and adjusted to pH 7.5 with aqueous solution of sodium bicarbonate. The organic layer was separated, washed with saturated aqueous solution of sodium chloride, dried over magnesium sulfate and concentrated in vacuo. The residue was pulverized with petroleum ether and collected by filtration to give t-butyl 7-(2-phenylacetamido)-3-hydroxymethylcepham-4-carboxylate (5.0 g.).

I.R. (Nujol): 3270, 1750, 1720, 1640 cm$^{-1}$
N.M.R. δ(DMSO—d$_6$, ppm): 1.45 (9H, s), 2.90 (2H, m), 3.55 (2H, s), 3.67 (2H, m), 4.47 (1H, m), 4.83 (1H, t, J = 5Hz), 5.03 (1H, d, J = 5Hz), 5.35 (1H, dd, J = 5Hz, 8Hz), 7.27 (5H, s), 9.07 (1H, d, J = 8Hz)

(2) N,N'-Dicyclohexylcarbodiimide (10.8 g.) and pyridine (1.4 g.) were added to a solution of t-butyl 7-(2-phenylacetamido)-3-hydroxymethylcepham-4-carboxylate (7.1 g.) in dimethylsulfoxide (30 ml.) and benzene (80 ml.). Trifluoroacetic acid (1.0 g.) was added dropwise to the stirred solution at room temperature and stirred overnight. The insoluble substance was filtered off and then ethyl acetate (100 ml.) and water (100 ml.) were added to the filtrate. After filtration, the organic layer was separated and adjusted to pH 3.0, washed with water and saturated aqueous solution of sodium chloride in turn, dried over magnesium sulfate and concentrated in vacuo. The residue was pulverized with petroleum ether to give t-butyl 7-(2-phenylacetamido)-3-formylcepham-4-carboxylate (7.0 g.)

I.R. (Nujol): 3270, 2110, 1760, 1730, 1650 cm$^{-1}$
N.M.R. δ(DMSO—d$_6$, ppm): 1.58 (9H, s), 3.20 (3H, m), 3.50 (2H, s), 5.0 (2H, m), 5.35 (1H, dd, J = 5Hz), 8Hz), 7.23 (5H, s), 8.93 (1H, d, J = 8Hz), 9.57 (1H, s)

(3) Anhydrous sodium acetate (1.0 g.) was added to a solution of t-butyl 7-(2-phenylacetamido)-3-formylcepham-4-carboxylate (2.0 g.) in acetic anhydride (5 ml.) and stirred at 65° to 70° C. for an hour. To the resultant solution were added water (200 ml.) and ethyl acetate (200 ml.), and adjusted to pH 8.0. The organic layer was separated, washed with aqueous solution of sodium chloride and dried over magnesium sulfate. The solution was concentrated in vacuo to give t-butyl 7-(2-phenylacetamido)-3-acetoxymethylenecepham-4-carboxylate (1.6 g.), mp. 178° to 183° C.

I.R. (Nujol): 3250, 1770, 1730, 1645 cm$^{-1}$
N.M.R. δ(CDCl$_3$, ppm): 1.43 (9H, s), 2.15 (3H, s), 3.40 (2H, AB—q, J = 15Hz), 3.60 (2H, s), 5.37 (1H, d, J = 5Hz), 5.50 (1H, s), 5.82 (1H, dd, J = 5Hz, 9Hz), 6.20 (1H, d, J = 9Hz), 7.28 (6H, s)

(4) Ozone gas was bubbled through a solution of t-butyl 7-(2-phenylacetamido)-3-acetoxymethylenecepham-4-carboxylate (1.9 g.) in ethyl acetate (16 ml.) and methanol (16 ml.). Dimethylsulfide (0.5 ml.) was added to the resultant solution and stirred at room temperature for 30 minutes. The resultant solution was added to ethyl acetate (200 ml.), washed with aqueous solution of sodium chloride, dried over magnesium sulfate and evaporated in vacuo. The residue was subjected to column chromatography on silica gel and eluted with a mixture of ethyl acetate and diisopropyl ether (1:5). The eluate was evaporated in vacuo to give t-butyl 7-(2-phenylacetamido)-3-hydroxy-3-cephem-4-carboxylate (0.83 g.).

I.R. (CHCl$_3$): 3410, 3310, 1773, 1724, 1672 cm$^{-1}$
N.M.R. δ(CDCl$_3$, ppm): 1.55 (9H, s), 3.35 (2H, AB—q, J = 12Hz), 3.66 (2H, s), 4.95 (1H, d, J = 4Hz), 5.34 (½H, s), 5.64 (1H, dd, J = 9Hz, 4Hz), 6.77 (1H, d, J = 9Hz), 7.34 (5H, s), 11.96 (½H, broad s)

EXAMPLE 2

Ozone gas was bubbled through a solution of t-butyl 7-(2-phenylacetamido)-3-acetoxymethylenecepham-4-carboxylate (0.5 g.) in methylene chloride (10 ml.) and ethanol (5 ml.) for 10 minutes at −60° C., and then the excess of ozone was removed by bubbling with nitrogen gas. To the resultant solution was added dimethylsulfide (0.16 ml.) at room temperature and stirred for an hour. Ethyl acetate (100 ml.) and water (200 ml.) were added to the solution, and the organic layer was separated, washed with water and aqueous solution of sodium chloride subsequently, and dried over magnesium sulfate. The solution was evaporated in vacuo to give t-butyl 7-(2-phenylacetamido)-3-hydroxy-3-cephem-4-carboxylate-1-oxide (0.35 g.).

I.R. (Nujol): 3250, 1780, 1720, 1660 cm$^{-1}$
N.M.R. δ(CDCl$_3$, ppm): 1.60 (9H, s), 3.67 (2H, s), 3.73 (2H, m), 4.50 (1H, m), 5.00 (1H, m), 7.13 (1H, m), 7.35 (5H, s)

EXAMPLE 3

(1) A suspension of palladium carbon (20 g.) in acetic acid (50 ml.) was added to a solution of 7-(2-phenylacetamido)-3-hydroxymethyl-2-cephem-4-carboxylic acid (19.0 g.) in acetic acid (150 ml.) and water (50 ml.). The solution was subjected to catalytic reduction in the presence of hydrogen gas of 20 kg./cm² at 70° C. for 5 hours. After filtration, the filtrate was concentrated in vacuo. The residue was dissolved in aqueous solution of sodium bicarbonate, washed with ethyl acetate, adjusted to pH 3.0 and then extracted with ethyl acetate. The extract was washed with aqueous solution of sodium chloride, dried over magnesium sulfate and evaporated in vacuo to give 7-(2-phenylacetamido)-3-hydroxymethylcepham-4-carboxylic acid (14 g.).

I.R. (Nujol): 3270, 1740, 1650 cm$^{-1}$
N.M.R. $\delta$(DMSO—d$_6$, ppm): 2.95 (2H, m),
3.58 (2H, s), 3.67 (2H, m),
4.58 (1H, m), 5.06 (1H, d,
J = 5Hz), 5.33 (3H, m), 7.33
(5H, s), 9.06 (1H, d, J = 8Hz)

(2) A solution of diphenyldiazomethane (4 g.) in ethyl acetate was added to a stirred solution of 7-(2-phenylacetamido)-3-hydroxymethylcepham-4-carboxylic acid (7.0 g.) in ethyl acetate (100 ml.) and tetrahydrofuran (20 ml.), and stirred at room temperature for an hour. After adding acetic acid to the resultant solution, the solution was concentrated in vacuo. The residue was subjected to column chromatography on silica gel, and then eluted with a mixed solvent of ethyl acetate and diisopropyl ether. The eluate was evaporated in vacuo to give diphenylmethyl 7-(2-phenylacetamido)-3-hydroxymethylcepham-4-carboxylate (2.5 g.).

I.R. (Nujol): 3250, 1740, 1660 cm$^{-1}$
N.M.R. $\delta$(CDCl$_3$, ppm): 2.73 (2H, m),
3.55 (2H, m), 3.70 (4H, m),
4.87 (1H, m), 5.13 (1H, d,
J = 5Hz), 5.83 (1H, dd, J = 5Hz,
8Hz), 6.93 (1H, s), 7.3 (15H,
m), 7.50 (1H, d, J = 8Hz)

(3) Dicyclohexylcarbodiimide (1.8 g.) and pyridine (0.23 g.) were added to a solution of diphenylmethyl 7-(2-phenylacetamido)-3-hydroxymethylcepham-4-carboxylate (1.5 g.) in dimethylsulfoxide (7 ml.) and benzene (15 ml.). To the solution was added trifluoroacetic acid (0.17 g.) and the mixture was stirred at room temperature overnight. After filtration, the filtrate was poured in a mixture of ethyl acetate (100 ml.) and water (100 ml.). The solution was adjusted to pH 3.0, and the ethyl acetate layer was separated, washed with aqueous solution of sodium chloride, dried over magnesium sulfate and concentrated in vacuo. The insoluble substance was removed by filtration and the filtrate was subjected to column chromatography on silica gel and eluted with a mixture of ethyl acetate and methylene chloride. The eluate was concentrated in vacuo to give diphenylmethyl 7-(2-phenylacetamido)-3-formylcepham-4-carboxylate (0.6 g.).

I.R. (Nujol): 3300, 1760, 1720, 1660 cm$^{-1}$
N.M.R. $\delta$(CDCl$_3$, ppm): 3.06 (2H, m), 3.57 (2H,
m), 5.13 (1H, d, J = 5Hz),
5.40 (1H, m), 5.65 (1H, dd,
J = 5Hz, 8Hz), 6.97 (1H, s),
7.00 (1H, m), 7.33 (15H, m),
9.58 (1H, s)

(4) Sodium acetate (0.23 g.) was added to a solution of diphenylmethyl 7-(2-phenylacetamido)-3-formylcepham-4-carboxylate (0.5 g.) in acetic anhydride (2 ml.), and stirred at 50° C. for 1.5 hours. The resultant solution was added to ethyl acetate (60 ml.) and water (50 ml.) and adjusted to pH 7.2 with sodium bicarbonate. The organic layer was separated, washed with aqueous solution of sodium chloride and dried over magnesium sulfate. The solution was evaporated in vacuo to give diphenylmethyl 7-(2-phenylacetamido)-3-acetoxymethylenecepham-4-carboxylate (0.4 g.).

I.R. (Nujol): 3300, 1760, 1740, 1685 cm$^{-1}$
N.M.R. $\delta$(CDCl$_3$, ppm): 2.10, 2.18 (3H, s, s,),
3.26 (2H, m), 3.62 (2H, s),
5.11-5.78 (3H, m), 6.40
(1H, m), 6.83, 6.90 (1H, s, s,),
7.3 (15H, m)

(5) Ozone gas was bubbled through a solution of diphenylmethyl 7-(2-phenylacetamido)-3-acetoxymethylenecepham-4-carboxylate (0.3 g.) in ethyl acetate (5 ml.) and methanol (5 ml.) at −60° C. Dimethylsulfide (0.1 ml.) was added to the resultant solution and stirred at room temperature for an hour. After concentrating the resultant solution in vacuo, the residue was subjected to column chromatography on silica gel and eluted with a mixture of ethyl acetate and diisopropyl ether. The eluate was concentrated in vacuo to give diphenylmethyl 7-(2-phenylacetamido)-3-hydroxy-3-cephem-4-carboxylate (0.09 g.).

I.R. (Nujol): 3340, 1760, 1660, 1630 cm$^{-1}$
N.M.R. $\delta$(CDCl$_3$, ppm): 3.28 (2H, m), 3.63
(2H, m), 5.08 (2H, m), 5.67
(1H, m), 6.53 (1H, m), 6.90
(1H, s), 7.33 (15H, m)

EXAMPLE 4

(1) 4-Nitrobenzyl bromide (1.64 g.) and triethylamine (0.73 g.) were added to a solution of 7-(2-phenylacetamido)-3-hydroxymethylcepham-4-carboxylic acid (2.0 g.) in dimethylsulfoxide (20 ml.) and stirred at room temperature for an hour. The resultant solution was poured into a solution of water (200 ml.) and ethyl acetate (200 ml.), and the organic layer was separated. Water (200 ml.) was added to the organic layer and then adjusted to pH 7.5 with an aqueous solution of sodium bicarbonate. The organic layer was separated, washed with water and a saturated aqueous solution of sodium chloride in turn, dried over magnesium sulfate and concentrated under reduced pressure. The residue was pulverized with diisopropyl ether to give 4-nitrobenzyl 7-(2-phenylacetamido)-3-hydroxymethylcepham-4-carboxylate (2.1 g.).

I.R. (Nujol): 3250, 1750, 1740, 1655, 1600 cm$^{-1}$
N.M.R. $\delta$(CDCl$_3$, ppm): 2.60 (2H, m), 3.17
1H, m), 3.60 (2H, s), 3.70 (2H, m),
4.13 (1H, m), 4.87 (1H, m), 5.15
(1H, d, J = 5Hz), 5.28 (2H, s),
5.55 (1H, dd, J = 5Hz, 8Hz), 7.3
(6H, m), 7.50 (2H, d, J = 8Hz),
8.25 (2H, d, J = 8Hz)

(2) 4-Nitrobenzyl 7-(2-phenylacetamido)-3-hydroxycepham-4-carboxylate (1.5 g.) was added to a solution of dimethylsulfoxide (15 ml.) and acetic anhydride (15 ml.), and stirred at room temperature for 5 hours. After adding the resultant mixture into water, ethyl acetate was added to the solution, adjusted to pH 7.5 and stirred for an hour. The ethyl acetate layer was separated, washed with a saturated aqueous solution of sodium chloride and dried over magnesium sulfate. The solution was concentrated under reduced pressure, and the residue was subjected to column chromatography on silica gel with a solution of diisopropyl ether and ethyl acetate (5:1) to give 4-nitrobenzyl 7-(2-phenylacetamido)-3-acetoxymethylenecepham-4-carboxylate (660 mg.).

I.R. (CHCl$_3$): 3340, 1768, 1744 (shoulder), 1674, 1601 cm$^{-1}$
N.M.R. δ(CDCl$_3$, ppm): 2.06 (3H, s), 3.45, 3.75 (2H, AB—q, J = 14Hz), 3.59 (2H, s), 4.56 (1H, s), 5.13 (1H, d, J = 6Hz), 5.25 (2H, s), 5.57 (1H, dd, J = 6Hz, 12Hz), 6.64 (1H, d, J = 12Hz), 7.30 (5H, s), 7.50, 8.25 (4H, AB—q, J = 12Hz), 4.68, 5.28 (1H, m)

(3) A solution of 4-nitrobenzyl 7-(2-phenylacetamido)-3-acetoxymethylenecepham-4-carboxylate (1.97 g), ethyl acetate (30 ml) and methanol (7.5 ml) was treated with ozone in a similar manner to that of Example 1 (4) to give 4-nitrobenzyl 7-(2-phenylacetamido)-3-hydroxy-3cephem-4-carboxylate (400 mg.).

I.R. (CHCl$_3$): 3650, 1770, 1730, 1670, 1606 cm$^{-1}$
N.M.R. δ(CDCl$_3$, ppm): 3.1–3.7 (2H, m), 3.64 (2H, s), 5.16 (1H, d, J = 4Hz), 5.28 (1H, s), 5.32 (2H, s), 5.62 (1H, dd, J = 4Hz, 10Hz), 6.76 (1H, d, J = 10Hz), 7.35 (5H, s), 7.53, 8.30 (4H, AB—q, J = 10Hz)

EXAMPLE 5

7-(2-Phenylacetamido)-3-hydroxymethylcepham-4-carboxylic acid (4 g.), dimethylsulfoxide (20 ml) and acetic anhydride (20 ml.) were treated in a similar manner to that of Example 4 (2) to give 7-(2-phenylacetamido)-3-acetoxymethylenecepham-4-carboxylic acid (2 g.).

I.R. (Nujol): 3260, 1742, 1655 cm$^{-1}$
N.M.R. δ(DMSO—d$_6$, ppm): 2.16 (3H, s), 3.61 (2H, s), 3.78 (2H, m), 4.55 (1H, s), 5.07 (1H, d, J = 4Hz), 5.42 (1H, dd, J = 4Hz, 8Hz), 7.31 (5H, s), 9.17 (1H, d, J = 8Hz), 4.70, 5.15 (1H, m)

EXAMPLE 6

(1) A suspension of 10% palladium-carbon (30 g.) in acetic acid (300 ml.) was added to a solution of diphenylmethyl 7-(2-phenylacetamido)-3-hydroxymethyl-2-cephem-4-carboxylate (30.0 g.) in tetrahydrofuran (500 ml.) and ethanol (100 ml.), and the mixture was subjected to catalytic reduction under hydrogen pressure of 10 kg/cm$^2$ at 50°–55° C. for 4 hours. After removing the insoluble substance from the resultant mixture by filtration, the filtrate was concentrated under reduced pressure. Ethyl acetate (500 ml.) was added to a residue and adjusted to pH 7.5 with an aqueous solution of sodium bicarbonate. The organic layer was separated, washed with water and a saturated aqueous solution of sodium chloride in turn and dried over magnesium sulfate. The solution was concentrated under reduced pressure to give diphenylmethyl 7-(2-phenylacetamido)-3-hydroxymethylcepham-4-carboxylate (17 g.).

I.R. (Nujol): 3250, 1740, 1660 cm$^{-1}$
N.M.R. δ(CDCl$_3$, ppm): 2.73 (2H, m), 3.55 (2H, m), 3.70 (4H, m), 4.87 (1H, m), 5.13 (1H, d, J = 5Hz), 5.83 (1H, dd, J = 5Hz, 8Hz), 6.93 (1H, s), 7.3 (15H, m), 7.50 (1H, d, J = 8Hz)

(2) Acetic anhydride (20 ml.) was added to a solution of diphenylmethyl 7-(2-phenylacetamido)-3-hydroxymethylcepham-4-carboxylate (10.0 g.) in dimethylsulfoxide (20 ml.), and stirred at room temperature for 15 hours. The resultant solution was poured into a solution of water (400 ml.) and ethyl acetate (400 ml.). The organic layer was separated and adjusted to pH 7.5 with an aqueous solution of sodium bicarbonate. The organic layer was separated, washed with water and a saturated aqueous solution of sodium chloride in turn, and dried over magnesium sulfate. The solution was concentrated under reduced pressure to give diphenylmethyl 7-(2-phenylacetamido)-3-acetoxymethylenecepham-4-carboxylate (5.3 g.).

I.R. (Nujol): 3280, 1760, 1740, 1660 cm$^{-1}$
N.M.R. δ(CDCl$_3$, ppm): 2.12(s) ⎫
                                                    ⎬ 3H, 3.63 (2H, s),
                             2.18(s) ⎭
3.70 (2H, m), 4.63 (1H, s),
4.77(m) ⎫
               ⎬ 1H,
5.37(m) ⎭
5.17 (1H, m), 5.67 (1H, m),
6.58 (1H, m),
6.90(s) ⎫
              ⎬ 1H
6.97(s) ⎭
7.0 (15H, m)

EXAMPLE 7

Pyridine (1.2 g.) was added to a solution of phosphorus pentachloride (3.1 g.) in methylene chloride (30 ml.) at 5° to 7° C. and stirred at the same temperature for 30 minutes. To the solution was added 4-nitrobenzyl 7-(2-phenylacetamido)-3-acetoxymethylenecepham-4-carboxylate (5.4 g.) at −10° C., and stirred at the same temperature for 1.5 hours. Methanol (8 ml.) was added to the solution at −30° C. and stirred at 0° C. for 40 minutes. Water (10 ml.) and methylene chloride (50 ml.) were added to the solution and adjusted to pH 5.0 with an aqueous solution of sodium bicarbonate. The organic layer was separated, washed with water (30 ml×2) and adjusted to pH 7.5 with an aqueous solution of sodium bicarbonate. The organic layer was separated, washed with a saturated aqueous solution of sodium chloride, and dried over magnesium sulfate. After treating the solution with activated charcoal, the solution was evaporated under reduced pressure. The residue was pulverized with diisopropyl ether and the precipitates were collected by filtration to give 4-nitrobenzyl 7-amino-3-acetoxymethylenecepham-4-carboxylate (3.0 g.).

I.R. (Nujol): 3300, 1760, 1670 cm$^{-1}$
N.M.R. δ(DMSO—d$_6$, ppm): 2.08 (s),
2.16 (d, J = 2Hz) } 3H
3.64 (2H, m),
4.55 (m)
4.68 (s) } 1H
5.24 (2H, m), 5.35 (2H, s),
7.65 (2H, m),
8.22 (2H, d, J = 8Hz)

EXAMPLE 8

(1) Phosphorus oxychloride (1.7 g.), trimethylsilylacetamide (1 g.) and N,N-dimethylformamide (0.73 g.) were added to a suspension of 2-(2-aminothiazol-4-yl)-2-methoxyiminoacetic acid (syn isomer, 1.8 g.) in tetrahydrofuran (20 ml.) at 5° C. Thus obtained solution was added all at once to a solution of 4-nitrobenzyl 7-amino-3-acetoxymethylenecepham-4-carboxylate (2.9 g.) and trimethylsilylacetamide (5.4 g.) in tetrahydrofuran (30 ml) at −20° C., and the mixed solution was stirred at −10° to −15° C. for an hour. After adding water (10 ml.) at −30° C., the resultant mixture was poured into a solution of ethyl acetate (200 ml) and water (200 ml.), and adjusted to pH 7.5 with sodium bicarbonate. The organic layer was separated, washed with a saturated aqueous solution of sodium chloride and treated with activated charcoal. After concentrating the solution under reduced pressure, the residue was pulverized with diisopropyl ether and collected by filtration to give 4-nitrobenzyl 7-[2-(2-aminothiazol-4-yl)-2-methoxyiminoacetamido]-3-acetoxymethylenecepham-4-carboxylate (syn isomer, 2.7 g.).

I.R. (Nujol): 1760, 1740, 1670 cm$^{-1}$
N.M.R. δ(DMSO—d$_6$, ppm): 2.16 (s)
2.20 (s) } 3H
3.70 (2H, m), 3.86 (3H, s),
4.70 (m)
4.76 (m) } 1H
5.37 (2H, s), 5.43 (2H, m),
6.71 (s)
6.74 (s) } 1H
7.25 (2H, m), 7.75 (2H, m),
8.33 (2H, d, J = 8Hz), 9.60 (1H, m)

(2) Methanol (10 ml) and acetic acid (3 ml.) were added to a solution of 4-nitrobenzyl 7-[2-(2-aminothiazol-4-yl)-2-methoxyiminoacetamido]-3-acetoxymethylenecepham-4-carboxylate (syn isomer, 2.5 g.) in tetrahydrofuran (60 ml.). 10% palladium-carbon (0.5 g.) containing water (2 ml.) was added to a solution and the mixture was subjected to catalytic reduction under ordinary pressure for 3 hours. After removing the insoluble substance from the resultant mixture by filtration, the filtrate was concentrated under reduced pressure. Ethyl acetate and an aqueous solution of sodium bicarbonate were added to the solution and adjusted to pH 7.5. The insoluble substance was removed from the mixture. The aqueous layer was separated, adjusted to pH 5.0 and washed with ethyl acetate. The solution was adjusted to pH 3.0 and extracted with ethyl acetate. The extract was washed with a saturated aqueous solution of sodium chloride, dried over magnesium sulfate and treated with activated charcoal. After concentrating the solution under reduced pressure, the residue was pulverized with diisopropyl ether and collected by filtration to give 7-[2-(2-aminothiazol-4-yl)-2-methoxyiminoacetamido]-3-acetoxymethylenecepham-4-carboxylic acid (syn isomer, 0.27 g.).

I.R. (Nujol): 3300, 1750, 1670 cm$^{-1}$
N.M.R. δ(DMSO—d$_6$, ppm): 2.10 (s)
2.18 (s) } 3H
3.67 (2H, m),
4.50 (m)
4.67 (s) } 1H,
5.30 (2H, m),
6.72 (s)
6.75 (s) } 1H
7.30 (2H, m), 9.60 (1H, m)

What we claim is:
1. A compound of the formula:

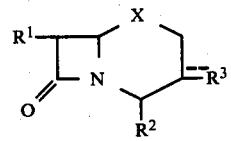

wherein R$^1$ is phenyl (lower) alkanoylamino, phenoxy (lower) alkanoylamino or aminothiazolyl (lower) alkanoylamino substituted with a lower alkoxyimino group,
R$^2$ is carboxy or a protected carboxy group,
R$^3$ is formyl, hydroxymethyl or acyloxymethylene, and
X is —S— or —SO—,
and its salt.

2. A compound of claim 1, wherein R$^1$ is phenyl (lower) alkanoylamino, phenoxy (lower) alkanoylamino or aminothiazolyl (lower) alkanoylamino substituted with a lower alkoxyimino group
R$^2$ is carboxy or an esterified carboxy group,
R$^3$ is formyl, hydroxymethyl or lower alkanoyloxymethylene, and
X is —S—.

3. A compound of claim 2, wherein R$^1$ is phenyl (lower) alkanoylamino, phenoxy (lower) alkanoylamino or aminothiazolyl (lower) alkanoylamino substituted with a lower alkoxyimino group,
R$^2$ is carboxy, lower alkoxycarbonyl, diphenyl (lower) alkoxycarbonyl or nitrophenyl (lower) alkoxycarbonyl,
R$^3$ is formyl or hydroxymethyl, and
X is —S—.

4. A compound of claim 3, which is, 7-phenylacetamido-3-hydroxymethylcepham-4-carboxylic acid.

5. A compound of claim 2, wherein R$^1$ is phenyl (lower) alkanoylamino, phenoxy (lower) alkanoylamino or aminothiazolyl (lower) alkanoylamino substituted with a lower alkoxyimino group,
R$^2$ is carboxy, lower alkoxycarbonyl, diphenyl (lower) alkoxycarbonyl or nitrophenyl (lower) alkoxycarbonyl,
R$^3$ is lower alkanoyloxymethylene, and
X is —S—.

6. A compound of claim 5, which is 7-phenylacetamido-3-acetoxymethylenecepham-4-carboxylic acid.

7. A compound of claim 5, which is 7-[2-(2-aminothiazol-4-yl)-2-methoxyiminoacetamido]-3-acetoxymethylenecepham-4-carboxylic acid (syn isomer).

8. A pharmaceutically antibacterial composition comprising a compound of claim 1 in association with a pharmaceutically acceptable, substantially non-toxic carrier or excipient.

9. A method for producing a pharmaceutical antibaterial composition which comprises mixing a compound of claim 1 as an active ingredient with an inert carrier.

* * * * *